United States Patent [19]
Damadian

[11] Patent Number: 6,165,139
[45] Date of Patent: *Dec. 26, 2000

[54] REMOTELY STEERABLE GUIDE WIRE WITH EXTERNAL CONTROL WIRES

[75] Inventor: Raymond V. Damadian, Woodbury, N.Y.

[73] Assignee: Fonar Corporation, Melville, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/457,506

[22] Filed: Jun. 1, 1995

Related U.S. Application Data

[62] Division of application No. 08/024,324, Mar. 1, 1993, Pat. No. 5,647,361.

[51] Int. Cl.⁷ ................................................ A61B 17/00
[52] U.S. Cl. .......................................................... 600/585
[58] Field of Search .................. 606/2, 3–18; 128/653.1, 128/653.2, 772; 600/585

[56] References Cited

U.S. PATENT DOCUMENTS

| | | |
|---|---|---|
| 3,470,876 | 10/1969 | Barchilon . |
| 3,625,200 | 12/1971 | Muller ...................................... 600/585 |
| 4,448,188 | 5/1984 | Loeb ............................................... 606/7 |
| 4,648,892 | 3/1987 | Kittrell et al. ............................ 606/12 |
| 4,729,384 | 3/1988 | Bazenet .................................... 606/585 |
| 4,921,482 | 5/1990 | Hammerslag et al. . |
| 4,957,481 | 9/1990 | Gatenby ............................. 128/665 X |
| 4,998,916 | 3/1991 | Hammerslag et al. . |
| 5,065,761 | 11/1991 | Pell .................................... 128/660.03 |
| 5,108,368 | 4/1992 | Hammerslag et al. . |
| 5,166,875 | 11/1992 | Machida .......................... 128/653.2 X |
| 5,174,297 | 12/1992 | Dalkuzuno .............................. 128/665 |
| 5,211,165 | 5/1993 | Dumoulin et al. ................... 128/653.1 |
| 5,290,266 | 3/1994 | Runling et al. .................. 128/653.2 X |
| 5,291,890 | 3/1994 | Cline et al. .......................... 128/653.2 |
| 5,322,508 | 6/1994 | Viera . |
| 5,372,587 | 12/1994 | Hammerslag et al. . |

*Primary Examiner*—David M. Shay
*Attorney, Agent, or Firm*—Morgan & Finnegan, LLP

[57] ABSTRACT

Patient treatment is carried out under magnetic resonance imaging (MRI) guidance. The treated region of anatomy may be a joint, an organ or other tissue, or a tumor. Instruments which can be guided by MRI allow the treated region of anatomy to be reached along a selected path, curved or straight, to reduce tissue injury. The delivery of treatments under MRI guidance and monitoring provides a method of identifying a preferred treatment regimen.

18 Claims, 7 Drawing Sheets

REMOTELY STEERABLE GUIDE WIRE WITH EXTERNAL CONTROL WIRES

CROSS-REFERENCE TO RELATED APPLICATIONS

The present application is a division of U.S. Ser. No. 08/024,324, filed on Mar. 1, 1993, which issued on Jul. 15, 2000 as U.S. Pat. No. 5,647,361.

BACKGROUND OF THE INVENTION

The present invention relates to improvements in magnetic resonance imaging, and more particularly to the development of treatment regimens and guidance of surgical procedures using magnetic resonance imaging.

The ability to produce excellent images of the internal anatomical structure of living beings using nuclear magnetic resonance signals has been well established. Magnetic resonance imaging is highly sensitive to the relaxation times of the nuclei emitting a magnetic resonance signal, and different relaxation times are manifested as different contrasts within the image. The tissues within the various organs and structures of a patient exhibit markedly different relaxation times. Diseased and injured tissue changes in relaxation time relative to healthy tissue. Consequently, MRI produces very high contrast images of anatomical structure, in which injured and diseased tissues are clearly delineated from normal tissue.

It would be highly desirable to have techniques for making available high quality MRI images for use by a surgeon throughout the course of a surgical procedure in order to display the progress of the procedure. Presently, MRI has been largely constrained to pre-operative and post-operative imaging. Additionally, MRI has been used to perform MRI-guided fine-needle aspiration cytology and MRI-guided stereotactic neurosurgery. Experiments are also being carried out using MRI to monitor the delivery of laser light for medical purposes. However, none of these procedures involve continuous monitoring of the surgical procedure, including instrument guidance and control during the course of the procedure, by MRI guidance.

It would be an important advance in the art to have the capability of guiding an entire surgical procedure by reference to updated MRI images of the region of anatomy being operated upon. Many surgical procedures require a large incision for the purpose of exposing the anatomical region upon which the surgery is to be performed to the view of the surgeon. The surgical treatment aspect of the procedure, however, may be very localized and involve much less cutting of tissue or other disruption than that which is caused by the entire procedure. Thus, any techniques which reduce the amount of tissue damage necessary to reach the surgical site would be important in the field of surgical treatment.

Conventional CT scanning has limited application in guiding surgical procedures. First, limitations on patient exposure to X-ray prevents the unlimited use of CT scanning on any particular individual patient. In addition, a surgeon and other surgical team members must not be subjected to the repeated exposure to X-rays that would result with repeated operations on successive patients. Additionally, soft tissue imaging with CT scanning requires the use of contrast agents, and in many cases this would involve repeated and prolonged administration of contrast agents to the patient during the course of the surgical treatment.

CT also suffers from artifacts such as those that occur at the interface of bone and soft tissue. Additionally, MRI easily images an oblique plane of the patient so that the image plane orientation can be selected and changed during the course of the surgical procedure, as required. CT studies are limited to around the transaxial plane and might require patient repositioning for some surgical procedures. Moreover MRI also permits full three dimensional (3D) acquisition of images which is ideal for surgery by MRI guidance.

Related copending patent application, Ser. No. 07/993,072 filed Dec. 18, 1992, and commonly assigned herewith, discloses nuclear magnetic resonance magnets and apparatus which are suitable for MRI-guided surgery and discloses carrying out surgery within such magnets under MRI guidance. It would be desirable to use MRI guidance to the maximum degree possible, in order to minimize patient tissue damage which is caused only for the purpose of reaching the anatomical site where the surgery is to be carried out.

Notwithstanding the excellent image quality, resolution and contrast achieved in MRI images, the MRI technique has not become an integral part of the development of treatment regimens, and the identifying and development of therapeutic chemicals. MR imaging is presently applied like other traditional radiological techniques, for obtaining images representative of tissue structure. Magnetic resonance images of different anatomical portions of a patient are obtained, and the images are interpreted by a radiologist whose interpretations are reported back to a treating physician. For example, images of the internal structure of a patient's brain are obtained, the radiologist examines them for the presence of lesions, malformations or other pathology, and his interpretation is reported to the treating physician, e.g. a neurologist. The neurologist then determines a course of treatment based upon the radiologist's interpretation and other signs acquired by the neurologist.

It would be highly desirable to use MRI to acquire images of the actual course of a treatment, and not just tissue condition before and after drug treatment. Images obtained during the course of treatment could be used to alter a surgical procedure or drug therapy and drug dosage during the treatment. This use of MRI could find application in the selection of therapeutic chemicals and the selection of dosage, the development and modification of treatment regimens and for the verification of diagnosis accuracy.

Accordingly, it is an object of the invention to provide improved surgical instruments for use in MRI-guided surgery.

Another object of the invention is to provide improved MRI guided surgical procedures.

Another object of the invention is to provide new methods using MRI for developing treatment regimens and therapeutic chemicals.

Yet another object of the invention is to provide specific procedures for MRI guided treatment of tumors.

SUMMARY OF THE INVENTION

According to the invention MRI guided invasive therapy is carried out by positioning a patient for the therapy and acquiring at least one magnetic resonance image of the anatomy of the region of the patient upon which the therapy is to be performed, while that patient is in position for the therapy. An instrument is introduced into the patient and guided to the region where the therapy is to be performed by reference to the magnetic resonance image during the course of the guiding, and then the therapy is carried out with the instrument. The instrument may be fitted at its end with a surgical tool, for cutting, electrocautery, delivery of laser light, delivery of ionizing radiation, or delivery of non-ionizing radiation (e.f. rf, microwave) or a catheter for the localized delivery of drugs. In a preferred embodiment the instrument is a surgical instrument having a movable end which can follow a curved path to a treatment site within a patient and which can be monitored for proper positioning by MRI.

In another preferred embodiment of the invention a treatment regimen is identified using MRI. A plurality of therapeutic chemicals are administered, not necessarily through the instrument, directly to a tumor within a patient, and the tumor is continuously monitored by repetitive magnetic resonance imaging after the administration of the therapeutic chemicals. The resulting magnetic resonance images are examined to determine the effectiveness of the respective therapeutic chemicals. The amounts of selected ones of the therapeutic chemicals are adjusted to improve therapy effectiveness.

BRIEF DESCRIPTION OF THE DRAWINGS

The objects, features and advantages of the present invention are readily apparent from the detailed description of the preferred embodiments set forth below, in conjunction with the accompanying drawings in which.

DETAILED DESCRIPTION OF THE PREFERRED EMBODIMENTS

Figure 1:
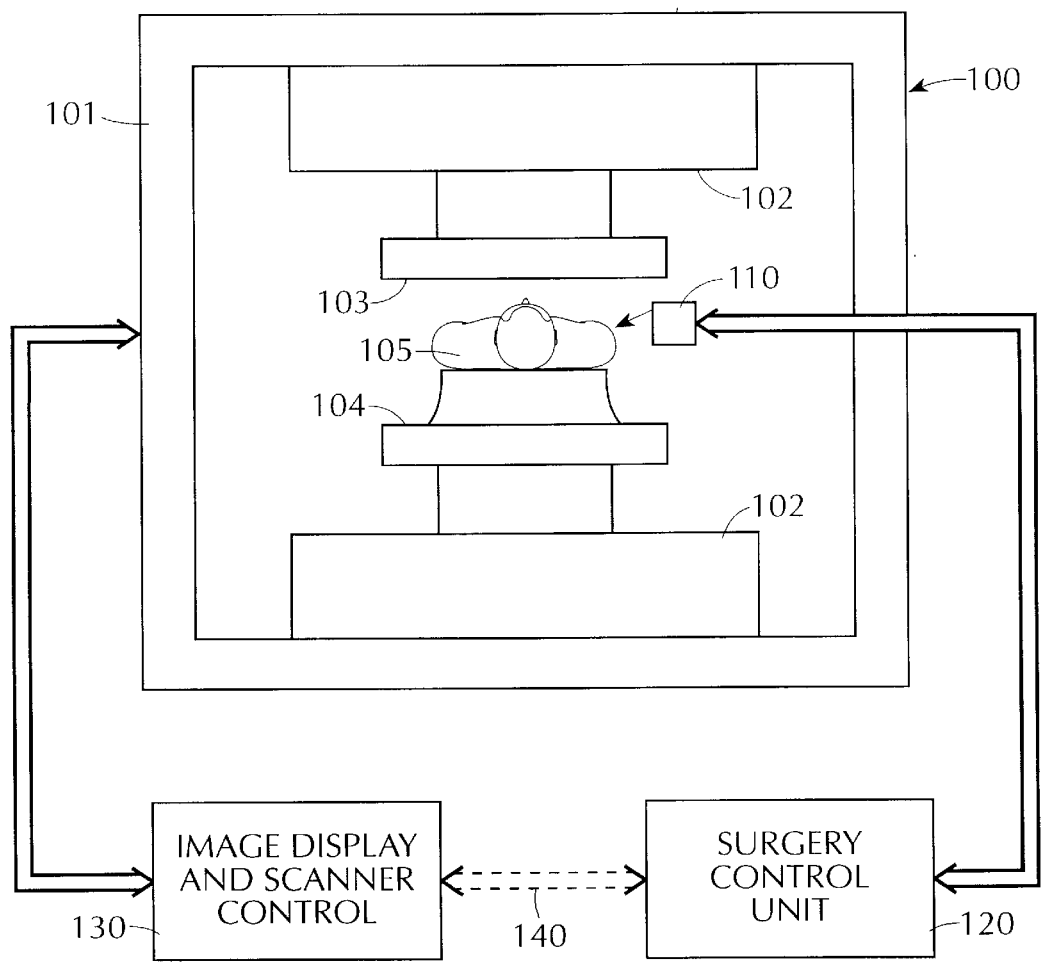
FIG. 1 illustrates an apparatus according to the invention for carrying out MRI-guided invasive treatment.

FIG. 1 illustrates an apparatus according to the invention for carrying out MRI-guided surgery. The apparatus includes a magnet 100 which is of the type disclosed in detail in copending U.S. application Ser. No. 07/993,072, filed Dec. 18, 1992 and commonly assigned. The detailed structure of the magnet is disclosed in the copending application. The magnet 100 is generally comprised of a ferromagnetic yoke 101 which provides a magnetic flux path for a magnetic flux generated by a source of magnetic flux 102. A pair of opposed pole surfaces 103, 104 define a gap 105 between them through which magnetic flux flows. A patient is positioned within the gap 105 for the acquisition of magnetic resonance imaging data, and to have surgical procedures carried out upon the patient under the guidance of the MRI images.

Block 110 represents means for performing surgery upon the patient. This structure can be dispensed with, and the surgery can be performed manually by a surgeon using appropriate surgical instruments. A preferred embodiment of the invention, and one of the novel features of the invention, utilizes a controllable apparatus for performing the surgery in lieu of manually performed surgery.

The surgery control unit 120 exercises control over the surgical performance unit 110 and receives position and other feedback signals for carrying out the surgical procedure. The surgical performance unit 110 is defined as the remote operating device wherein remote is defined as any region outside the body including all regions adjacent to the skin. The surgical performance unit can be either a manually operated or computer operated device for advancing the surgical instrument and/or therapeutic chemical delivery instrument into the patient's interior.

The scanner control unit and image display 130 interacts with the scanner magnet 100 and ancillary scanner subsystems for carrying out MRI on the patient and displaying the images on monitors for direct viewing. The scanner control unit and image display 130 can be used for carrying out repetitive scans during the course of the surgery to allow the surgeon and assisting personnel to continuously have current images of the anatomical site undergoing surgery on display to them.

The surgery control unit 120 and scanner control unit and image display 130 are shown as separate system elements, with a communication path 140 between them. In practice, these two units may be physically integrated such that they are operated from the same console and share operator controls and display screens. The surgery control unit 120 operated in concert with the scanner control unit enables the surgeon to plan the path of the surgical device from the outside of the patient towards the target tissue. The imaging display console may possess light pen capability so the surgeon may superimpose the line of the desired surgical path on the image or he may enter the path coordinates thru a keyboard. With the light pen path superimposed on the image the surgeon may then advance the surgical device (catheter, needle etc.) towards the target tissue and monitor its course with repeated images comparing the actual course with the planned light pen course to be certain the desired path is being achieved. However, they are functionally distinct and are separately represented in the drawing figure.

A novel feature of the present invention which is critical to carrying out generalized MRI-guided surgery is the provision of surgical instruments that can deviate from a linear path of travel through the human body while under MRI guidance. A preferred embodiment of such an instrument is shown in FIGS. 2A–2D.

Figure 2A:
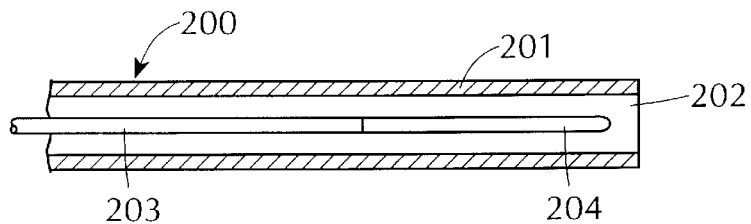
FIGS. 2A–2D illustrate the operation of a surgical instrument according to the invention for use in MRI-guided surgery.

A catheter and guide combination 200 shown in FIG. 2A is comprised of a tubular catheter body 201 having an open end 202. The open end 202 constitutes the leading end of the catheter body 201 which is inserted into the body of a patient. A guide wire 203 extends through the tubular catheter 201 along its length and is movable lengthwise through the catheter 201. The guide wire 203 terminates at a movable end portion 204 which is described below. The movable end portion 204 is the leading end of the guide wire 203 when it is advanced into the body of a patient.

The use of the catheter and guide structure is shown by the sequence of FIGS. 2A–2D. Initially the catheter 201 and guide wire 203 are straight. They are inserted into the patient's body as a pair and advanced together with the catheter open end 202 and the guide wire end portion 204 advancing together as the leading ends of the structure.

Figure 2B:
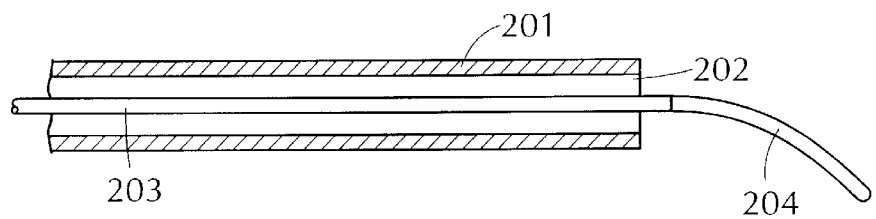

When it is desired to change the direction of advance of the catheter and guide wire the advancing of the catheter 201 is stopped while the guide wire 203 is advanced so that the guide wire end 204 extends beyond the open end 202 of the catheter 201. The end 204 of the guide wire 203 is caused to deflect toward the intended new direction of advance. This condition is shown in FIG. 2B.

Figure 2C:
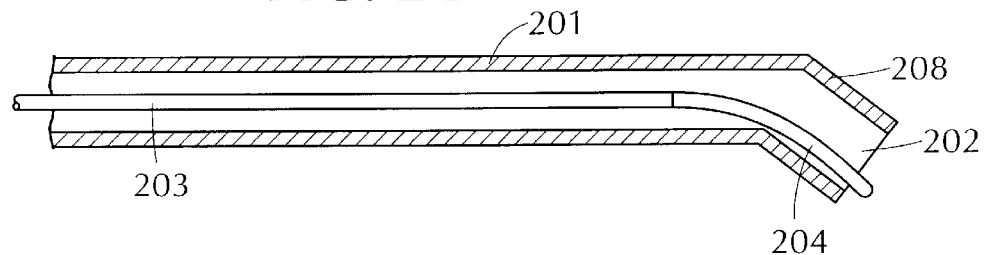

Advancement of the catheter 201 is then resumed with the open end 202 of the catheter following along the curved end portion 204 of the guide wire 203. The deflected end portion 204 causes the advancing catheter 201 to change direction as it advances with a result that a bent portion 208 is induced in the normally straight catheter 201. This condition is shown in FIG. 2C.

Figure 2D:
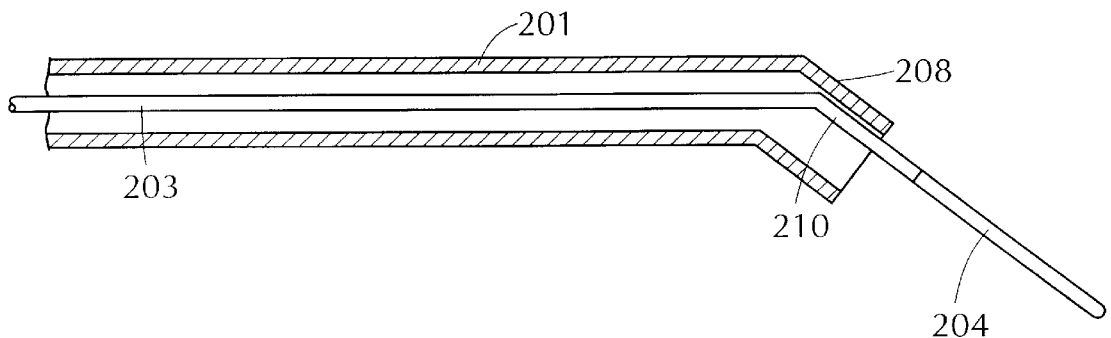

Next, the guide wire 203 is advanced in the new direction. The catheter 201 is surrounded by body tissue so that the bend 208 will not relax and straighten, even after the end portion 204 of the guide wire is advanced out through the open end 202 of the catheter 201. Consequently, as the guide wire 203 is advanced into the patient's body it will change direction at a bend 210 which is a result of the guide wire advancing against the bent portion 208 of the catheter 201. This is shown in FIG. 2D.

If the tissue surrounding the catheter is sufficiently firm, the catheter can be advanced along with the guide wire without losing the change of direction achieved by the bent portion 208 of the catheter 201. Both the catheter 201 and the guide wire 203 should be resilient so that they can be bent, and so they will also return to their relaxed shape after any bending pressure has been removed. They must likewise be sufficiently stiff to allow them to be advanced axially by pushing on them at a location remote from the advancing end. Finally, the guide wire 203 should be nonferrous to avoid image artifacts caused by magnetic field homogeneity.

Figure 3:
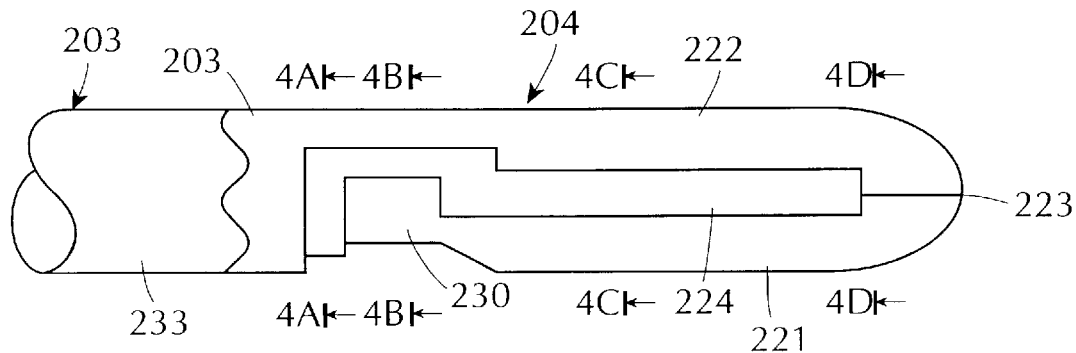
FIG. 3 illustrates details of the movable end of the surgical instrument shown in FIG. 2.

Details of the movable end portion 204 of the guide wire 203 are shown in FIG. 3. The movable end portion 204 is shown in longitudinal section and is comprised of a bimetallic structure having a lower 221 and an upper half 222. Lower half 221 and upper half 222 are each made from a different metal having a different coefficient of thermal expansion. The halves 221, 222 meet at a permanent junction 223 at the free end of the movable end portion 204.

A thin insulative layer 224 is disposed between the metal halves 221 and 222 of the movable end 204, except at the junction 223. For purposes of illustration the insulative layer 224 is shown thicker than it would be made in practice. The guide wire 203 is comprised of a coaxial conductor for providing a current path to the movable end 204. The center conductor 230 of the guide wire is fused to the bottom half 221 of the movable end portion. An inner insulator 231 connects with the insulative layer 224 and also serves to insulate the center conductor 230 of the guide wire from the outer conductor 232. The upper half 222 of the movable end is fused to the outer conductor 232 of the guide wire, and the guide wire is covered by an outer insulative layer 233.

The structure of the movable end portion 204 of the guide wire 203 results in a series circuit for flowing current through the bimetal structure of the movable end portion 204. In particular, current flows through the center conductor 230 of the guide wire into the lower half 221 of the movable end portion and through the junctioned 223. The current continues through the upper half 222 of the movable end portion and back through the outer conductor 232 of the guide wire. The insulative layer 224 insures that current flows through the entire length of the bimetallic structure of the movable end portion for heating the two metal halves 221, 222 and maximizing the deflection which will occur because of their different respective thermal coefficients of expansion.

Figure 4A:
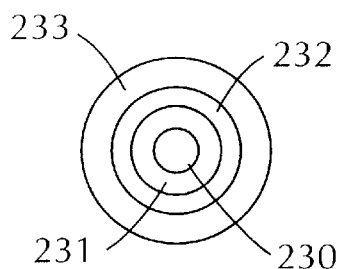
FIGS. 4A–4D are cross sections of the movable end of the instrument shown in FIG. 3.
Figure 4C:
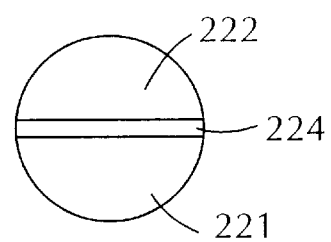
Figure 4B:
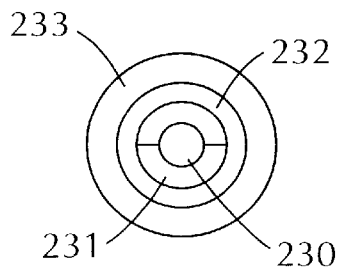
Figure 4D:
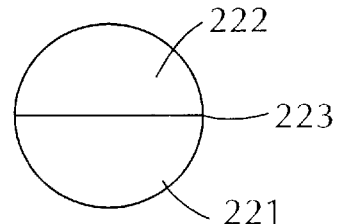

The cross-sectional structure of the movable end portion along the successive section lines in FIG. 3 is illustrated in FIGS. 4A–4D. FIG. 4A shows the concentric structure of the guide wire comprising the central conductor 230 and the outer coaxial conductor 232 with the intermediate insulating layer 231 between them. FIG. 4B shows the cross-sectional structure at the junction between the movable end 204 and the guide wire 203. FIG. 4C is a cross section through the movable end portion 204 and shows the position of the insulative layer 224 between the metallic halves 221 and 222. Finally, FIG. 4D is a cross section through the junction 223 of the two metal halves 221 and 222.

A method of fabricating the movable end portion 204 is shown in FIGS. 5A–5E. The starting components for the fabrication of the movable end portion include an upper blank 301 and a lower blank 302 shown in FIGS. 5A and 5B, respectively. The upper blank 301 has a T-shaped end 303 and is shown edgewise in the figure. The lower side of the upper blank 301 has an insulative layer 304 disposed on it. The upper blank 301 will become the upper half 222 of the movable end portion, and the insulative layer 304 will become the insulative layer 224 which is between the two halves of the movable end portion 204. The insulative layer 304 is advantageously formed by a conventional anodizing process so that it will be continuous but only a few molecules thick, and tightly adherent to the upper blank 301. Alternatively, the insulative layer 304 can be a resilient adhesive. The layer 304 is not coextensive with the length of the top blank. End portions 305 and 306 of the under side of the upper blank 301 are both free of the insulative layer 304. Region 304 is the site where the bond 223 will be formed, and region 306 is the site where the junction between the movable end portion 204 and the guide wire 203 will be formed.

Figure 5A:
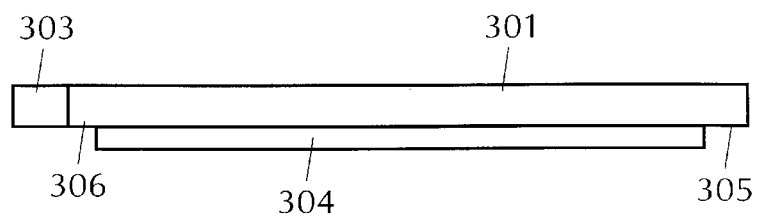
FIGS. 5A–5E illustrate the steps in fabricating the movable end of the instrument shown in FIG. 3.
Figure 5B:
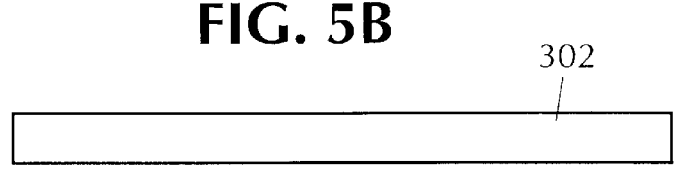

The lower blank 302 shown in FIG. 5B is somewhat shorter than the upper blank. The lower blank 302 is made of a metal different than that of the upper blank 301, and the metal comprising the lower blank 302 has a different coefficient of thermal expansion than the upper blank 301.

Figure 5C:
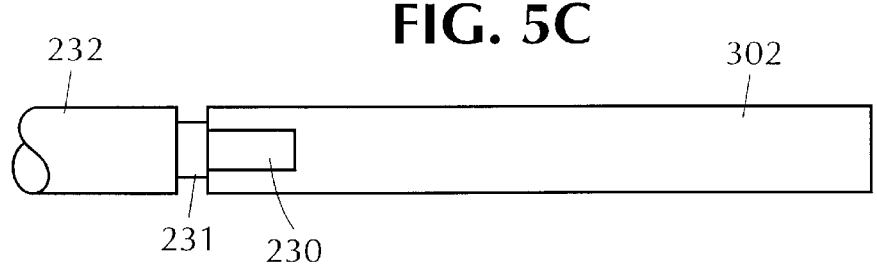
Figure 5D:
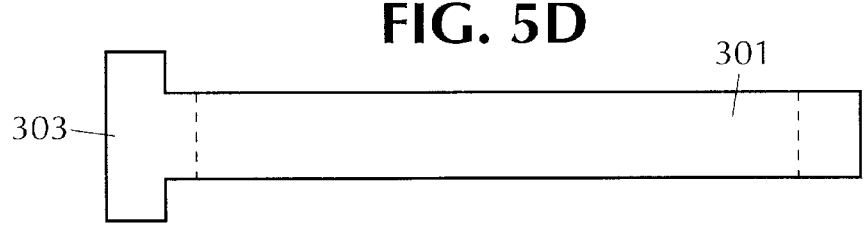

FIG. 5C is a plan view showing the lower blank 302 and the guide wire 303 positioned prior to the formation of the movable end portion 304. The center conductor 230 of the guide wire is exposed and partially overlying the end of the lower blank 302. Part of the inner insulator 231 is also exposed, and the outer conductor 232 of the guide wire 203 is exposed. The upper blank 301, shown in plan in FIG. 5D is next placed above the lower blank 302 with the T-shaped end 303 overlying the outer conductor 232 of the guide wire. This arrangement of parts is shown in FIG. 5E.

Figure 5E:
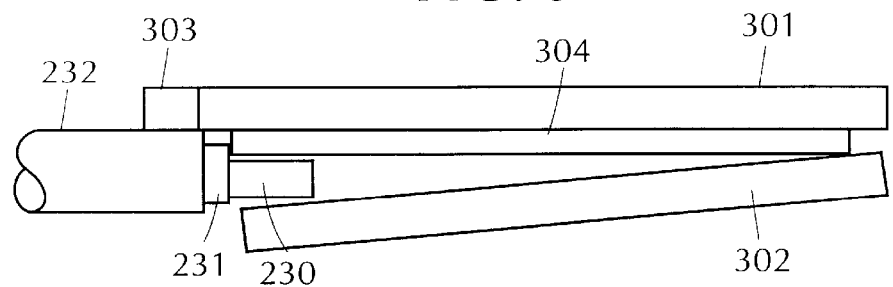

Next, the combination of elements shown in FIG. 5E is compressed and a percussive weld or bond is formed at the ends of the upper and lower blanks 301, 302 which are distant from the guide wire 203. This creates the junction 223. The upper and lower blanks 301, 302 are squeezed adjacent to each other and a percussive bond or weld is formed between the lower blank 302 and the center conductor 230 of the guide wire. Finally, the T-shaped end 303 of the upper blank is bent or swaged downward and bonded to the underlying part of the outer conductor 232 of the guide wire. The resulting structure is the movable end portion 204, and its final shaping is completed by etching and polishing finishing steps.

Figure 6:
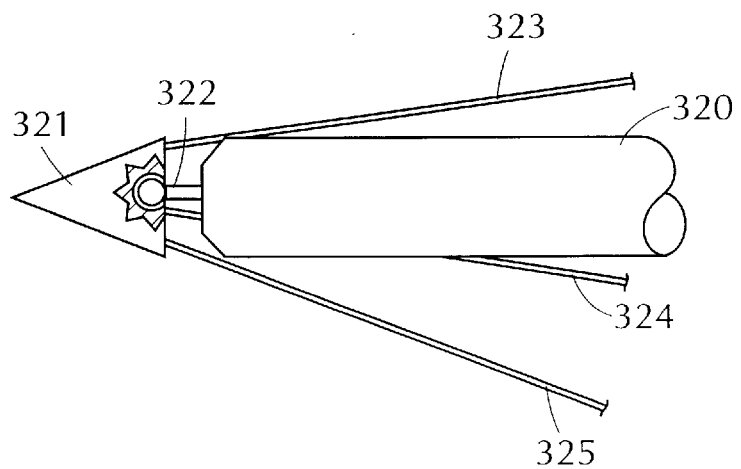
FIG. 6 illustrates another embodiment of a movable end of the instrument according to the invention.

Another embodiment of the guided instrument according to the invention is shown in FIG. 6. The instrument is comprised of a guide wire 320 having a conical head 321 mounted on one end of the guide wire. A pivot 322 mounts the head 321 for pivotal movement relative to the longitudinal axis of the guide wire 320. A plurality of control wires 323, 324 and 325 are disposed around the periphery of the head 321. Applying tension to one or more of the guide wires 323–325 is effective to pivot the head 321 on the pivot 322. Selective application of tension to different control wires allows the head 321 to be oriented in a controllable fashion. The illustrative embodiment has three control wires 323–325, but the number of control wires could be increased. The illustrative embodiment can be used with a catheter as in the previously described embodiment, or the catheter can be dispensed with. Surrounding tissue will be effective to hold the control wires 323–325 next to the guide wire 320 as the instrument advances through the tissue of a patient.

Figure 7A:
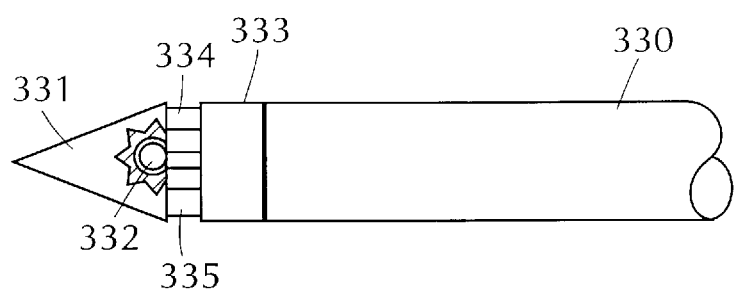
FIGS. 7A and 7B illustrate a third embodiment of a movable end of the instrument according to the invention.
Figure 7B:
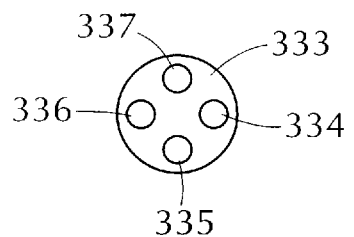

Another embodiment of the instrument according to the invention is shown in FIGS. 7A and 7B. The guide wire 330 has at one end thereof a head 331 mounted by a pivot 332 on a base 333. The base 333 is fixed to the guide wire 330. A plurality of piezoelectric actuators 334, 335, 336 and 337 are disposed around the circumference of the base 333 and between the base 333 and the head 331. The layout of the piezoelectric actuators is shown in FIG. 7B.

By applying voltages to different actuators the orientation of the head 331 is varied in a pivotal motion relative to the longitudinal axis of the guide wire 330. Conductive paths extending through the guide wire 330 can provide individual voltages to the respective piezoelectric actuators to allow them to be energized independently. This embodiment of the invention is particularly advantageous because the actuating signal, an electrical voltage, can be set to a very high degree of precision and the resulting displacement of the head 331 relative to the guide wire 330 can be determined very precisely.

In a preferred embodiment, the instrument according to the invention includes a material which will give a strong MRI signal so that the instrument will appear prominently in magnetic resonance images. The instrument could comprise a tip which is paramagnetic, or alternatively the instrument tip could be opaque to MRI. The position of the instrument in a magnetic resonance image of the instrument and surrounding anatomy will appear correct relative to the surrounding anatomy. The instrument within a small region of interest or field of view can advantageously be imaged more frequently than the entire anatomy of interest, and the instrument image can be updated more frequently, to allow the instrument motion to be tracked by MRI.

The display for displaying a magnetic resonance image of the anatomy to be treated can include means for receiving a representation of the path to be followed by the instrument. The means for receiving a path representation can include a cathode ray tube for displaying the magnetic resonance image together with a light pen system which will allow the intended instrument path to be drawn on the displayed image. The advance of the instrument during the course of treatment is displayed to allow comparison between the planned and actual instrument path, and correction or adjustment of the instrument path as needed.

The catheter and guide wire previously described can be used for carrying out various methods according to the present invention. The catheter and guide wire combination are advanced through a patient to a treatment site in the manner previously established. The guide wire is then withdrawn leaving the catheter in place, and any of a variety of treatments using the catheter can be commenced.

The catheter can be used for the direct delivery of a therapeutic chemical to the treatment site. The treatment site can be a tumor, or a tissue containing a tumor, as well as a site where a surgical treatment is to be carried out. The therapeutic chemical can be delivered in an unactivated state, or as an active therapeutic chemical. Activation of the therapeutic chemical can be carried out in vivo by an appropriate means. For example, the therapeutic chemical may comprise a porphrin such as protoporphyrin which can be activated in vivo by light. The therapeutic chemical is first introduced, for example, into a tumor, through the catheter, and then an optical fiber is extended through the catheter into the tumor for directing light to the protoporphyrin. High intensity laser light is delivered through the optical fiber to activate the protoporphyrin within the tumor.

Another important embodiment of the invention includes the delivery of a therapeutic chemical to a tissue containing a tumor. In particular, the introduction of antioxidants into the tissue, followed by continuous monitoring in the form of repetitive magnetic resonance imaging is used to evaluate the efficacy of the antioxidant. This method may be carried out with the further step of introducing the antioxidant directly into the tumor and simultaneously delivering a therapeutic chemical for treatment of the tumor directly into the tumor. Suitable antioxidants include a tocopherol (Vitamin E), butylated hydroxy toluene, and carotene.

Another method according to the invention is a method for identifying a treatment regimen. This is carried out by administering a therapeutic chemical directly to a tumor within a patient, and continuously monitoring the tumor by repetitive magnetic resonance imaging to determine the efficacy of the therapeutic chemical. Based on the determined efficacy the amount of therapeutic chemical administered is adjusted to improve the effectiveness of the treatment carried out with the therapeutic chemical.

The method just described can be augmented by administering a second therapeutic chemical, (and subsequent therapeutic chemicals), directly to the tumor within the patient after the efficacy of the first administered therapeutic chemical has been determined. The tumor is continuously monitored by repetitive magnetic resonance imaging after administration of the second (or subsequent) therapeutic chemical to determine the efficacy of the latter administered therapeutic chemical. The amount of the second therapeutic chemical is likewise adjusted based on the determined efficacy in order to improve the treatment.

A variation of the methods just described is carried out by administering a plurality of therapeutic chemicals directly to separate regions of the same tumor within a patient. The tumor is continuously monitored by repetitive magnetic resonance imaging after the administration of the therapeutic chemicals to determine the effectiveness of the treatment. Thereafter, the administered amounts of selected therapeutic chemicals are adjusted to improve the treatment. In another embodiment of this method, one or more of the administered therapeutic chemical are selected for ongoing treatment of the tumor.

In another embodiment, oxygen is delivered as a therapeutic chemical. The delivery of oxygen is also used for determining the degree of tissue oxygenation. The tissue is imaged and then oxygen is delivered to the tissue by direct perfusion with gaseous oxygen or by administering the oxygen in combination with an oxygen carrier molecule such as hemoglobin or heme. After the administration of oxygen the tissue is imaged again and the contrast of the two images is compared. The change in image contrast is a measure of the initial degree of oxygenation of the tissue.

Image contrast also provides a measure for determining the uptake of administered therapeutic chemicals, and the uniformity of distribution of a chemical within an organ or a particular target tissue. The ability to monitor the uptake of an administered therapeutic chemical permits the development of treatment regimens involving systemic delivery of the therapeutic chemical. Moreover, image contrast permits determination of a desired degree of tissue perfusion and allows correct dosage of a therapeutic chemical to be selected.

Where the target tissue to be treated is a tumor, a preferred embodiment of the invention includes imaging the tumor by three dimensional (3D) imaging. The invention is not limited to a particular type of tumor, but includes the treatment of hepatic, pancreatic, breast, colon, lung, brain, bone, prostate, ovarian, uterine, kidney, stomach, head, neck, testicular and neurological tissue tumors, and tumors in other tissue and organs. Moreover, the treatment method is not limited to the delivery of a therapeutic chemical, and the instrument according to the invention includes instruments having means for delivering various treatment agents including heat, light or radiation, as well as a therapeutic chemical. The instrument may also include means for excising tissue.

Figure 8:
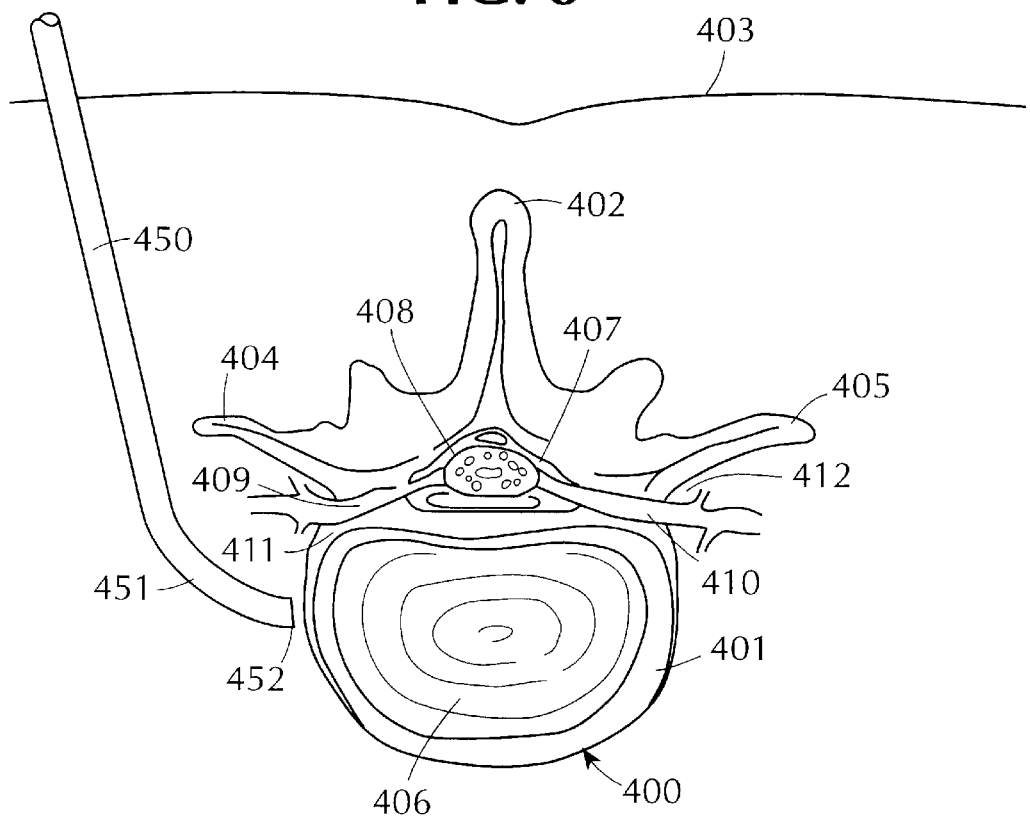
FIG. 8 is an anatomical drawing of a human lumbar vertebra showing a catheter implanted for carrying out MRI guided treatment.

The surgical treatment of the spine provides a good example of the utility of the method according to the invention carried out with the instruments according to the invention. FIG. 8 shows a vertebra of the lumbar spine of a human together with the spinal cord and the spinal nerve roots in situ.

The lumbar vertebra 400 is comprised of a vertebral body 401 and various associated processes. The spinous process 402 is a central bony protrusion which extends posteriorly towards the patient's back 403. The transverse processes 404, 405 extend transversely relative to the spinous process 402 and the axis of the spine. The intervertebral disc 406 is a generally disc-shaped body of fibrous material disposed between and attached to the vertebral body 401 of vertebra 400 and the vertebral body of the next adjacent vertebra (not shown). The vertebral foramen 407 is an opening surrounded by the spinous process 402 and the transverse processes 404, 405 and through which the spinal cord 408 extends. The spinal nerve roots 409, 410 branch from the spinal cord 408 and each extends through an intervertebral foramen 411 and 412, respectively, to exit the spine.

Herniation of the disc 406 can apply pressure to a nerve root 409 or 410. This condition can be extremely painful and frequently requires surgical treatment. Conventionally, the procedure for surgery upon a herniated disc involved cutting and displacement of the extensive spinal musculature around the affected disc in order to expose the herniation for surgical treatment. In addition, a substantial part of the bone posterior of the vertebral foramen including the spinous process may have to be cut away and removed.

In the method according to the present invention, the surgical treatment is carried out under MRI guidance with instruments according to the invention in order to avoid the extensive cutting of tissue which occurs in conventional surgery. An advantage of MRI guidance is the freedom to view the region of anatomy where surgery is to be performed from an arbitrary orientation selected based on anatomical and procedural considerations. An additional advantage of MRI is its unique capability to provide full 3D visualization.

A preferred embodiment of spinal surgery includes the selection of an image plane or slice such that an entire spinal nerve root lies within an imaged slice, or in a related embodiment the entire nerve root and surrounding intervertebral foramen lie within the imaged slice. In either case, the imaged slice is oblique to the axis of the spine because the spinal nerve roots are not perpendicular to the spine axis. The spinal nerve roots leave the spine at acute angles which vary from vertebra to vertebra. Although the spinal nerve roots 409, 410 in FIG. 8 appear in the plane of the drawing, in reality they recede from the drawing plane.

Figure 9:
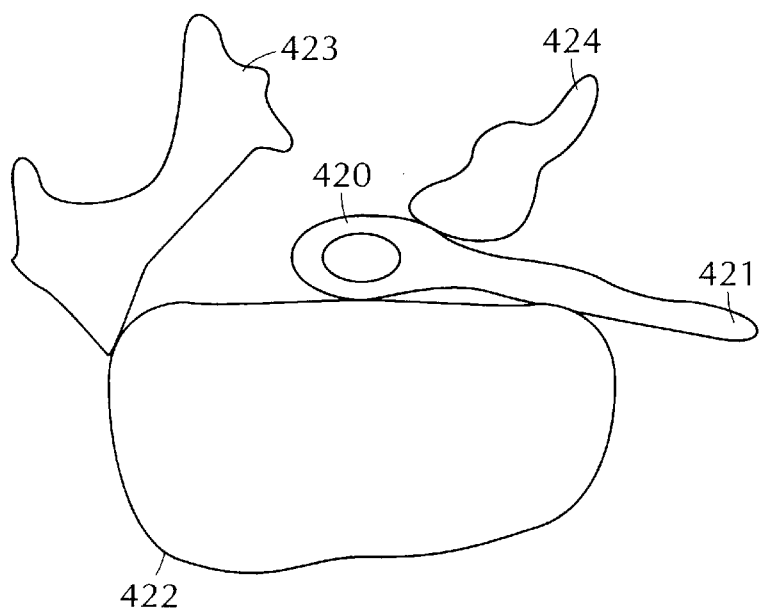
FIG. 9 is a drawing of a magnetic resonance image of an anatomical model of a human lumbar spine with the spinal nerve root lying wholly within the image slice.

FIG. 9 is made from a magnetic resonance image of an anatomical model of the human lumbar spine. The spinal cord 420 having spinal nerve root 421 is situated posterior to the image region 422. Because the imaged slice is oblique to the spinal axis, it intersects adjacent vertebral bodies which appear in the image as the region 422. Also, because the imaged slice is only a few millimeters thick and is oblique relative to the spinal axis, only the single nerve root 421 is seen in the image. The nerve root 421 lies wholly within the imaged slice. Processes 423 and 424 above the vertebral body 422 are from adjacent vertebra because of the oblique orientation of the imaged slice. The important feature to note in this image is that the spinal nerve root 421 fully visualized in its canal despite the fact that it runs obliquely in the body and is achieved bacause of the MRI's capability to orient its slices at any angle unlike the CAT scan and other medical imaging modalities. The spinal nerve is unobstructed by any disc protrusions in its course through the canal.

Figure 10:
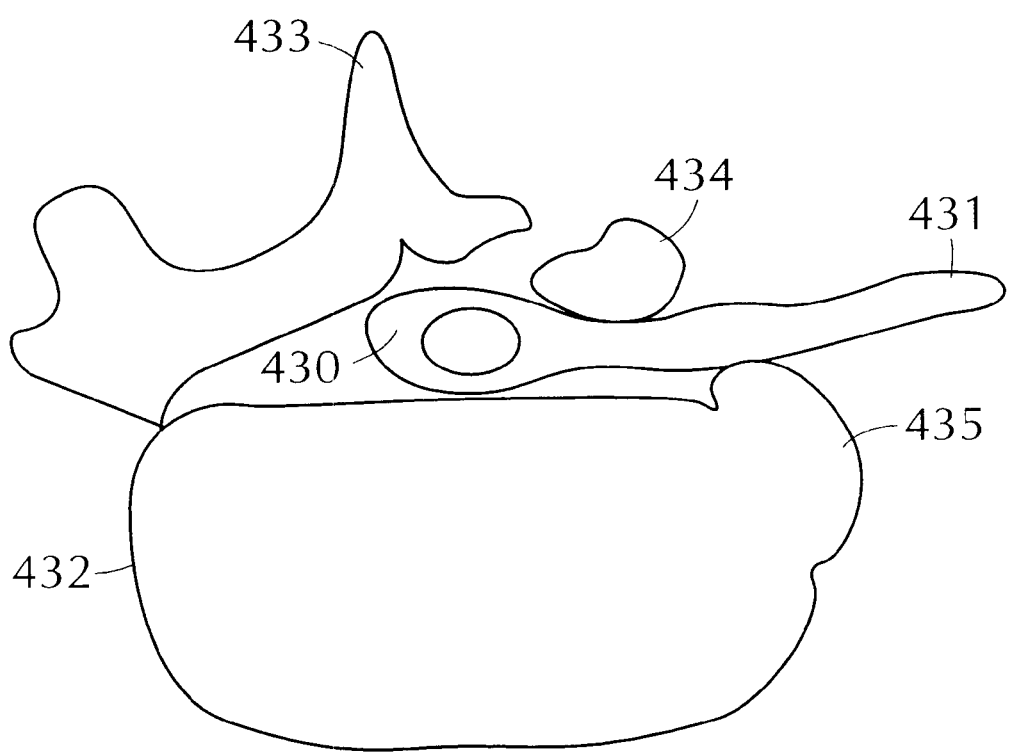
FIG. 10 is another drawing of a magnetic resonance image of an anatomical model of a human lumbar spine oriented as in FIG. 9 and showing a herniated intervertebral disc.

FIG. 10 is also made from a magnetic resonance image of an anatomical model of the human lumbar spine in which a spinal nerve root lies wholly within the imaged slice. The spinal cord 430 and spinal nerve root 431 lie posterior to image region 432, which is a slice through adjacent vertebral bodies and intervertebral disc. Processes 433 and 434 lie above the spinal cord and spinal nerve root. Region 435 of the image is where the imaged slice passes through a bulge in a herniated intervertebral disc.

The bulging region 435 of the disc impinges on the spinal nerve root 431 and tends to displace it away from the vertebral body and toward the processes that are posterior to the vertebral body. In the imaged anatomical model shown in FIG. 10, the pressure from the bulge causes a displacement of the spinal nerve root 431. In a living human, however, the spinal nerve root is embedded within tissue and it cannot be displaced without deformation. A bulging herniated disc will consequently compress the spinal nerve root upon which it impinges and cause pain. Surgery is required to remove the bulge and relieve the pressure on the nerve root. According to the invention, surgical treatment of the herniated intervertebral disc, is carried out under MRI guidance.

Referring back to FIG. 8, a catheter 450 extends through the back 403 of a patient and terminates adjacent the disc 406. The catheter is more or less straight for part of its length, but has a sharply bent portion 451 so as to undergo a marked change of direction such that the catheter end 452 is adjacent the disc 406. When viewing the figure it must be kept in mind that the catheter 450, like the nerve roots 409, 410 is not in the plane of the drawing over its entire length, and the catheter 450 may approach the intervertebral disc along a direction form either above or below the drawing plane.

The catheter 450 is implanted using any of the previously described instruments, which enable the direction change at the bent position 451. As a consequence, the path of the instrument and the catheter can start at a region of the back close to the spine and the instrument and catheter can be advanced through the patient in a direct, and short, path to the spine. At some position close to the spine the direction of the instrument is changed sharply to position the catheter end 452 adjacent the tissue which is to undergo surgical treatment, in this case the disc. When it is implanted the catheter provides a path for surgical access to the treatment site and removal of tissue.

This technique allows spinal surgery to be carried out with a substantial reduction in overall tissue injury that is inherent in conventional macrosurgery. Moreover, surgery can be carried out below the posterior processes, and even In the intervertebral foramen, without having to remove or alter any of the bony processes of the spine such as would occur in a laminectomy.

I claim:

1. A remotely controlled guide wire comprising:

a central wire extending substantially the length of said remotely control guide wire, the central wire having a distal end;

a conical head pivotally connected to and extending from the distal end of the central wire, the conical head having a solid exterior surface; and means coupled to the conical head for changing the direction of the conical head, the means being external to the central wire along the entire length of the central wire.

2. A remotely controlled guide wire comprising:

a guide wire having a distal end;

a conical head pivotally connected to and extending from the distal end of the guide wire; and a plurality of outer wires connected to the conical head and extending along the entire length of the guide wire, the outer wires being external to the central wire along the entire length of the guide wire, for changing the direction of the conical head by the selective application of tension to at least one of the wires.

3. The remotely controlled guide wire of claim 2, wherein the guide wire has a larger diameter than the outer wires.

4. The remotely controlled guide wire of claim 2, wherein the guide wire is hollow.

5. The remotely controlled guide wire of claim 2, wherein the distal end of the conical head has a sharp end.

6. The remotely controlled guide wire of claim 2, further comprising means for establishing the position of the distal end of the guide wire within a patient by magnetic resonance imaging.

7. The instrument of claim 2, wherein the conical head has a solid exterior surface.

8. An instrument comprising:

a catheter shaft;

a guide wire received within the catheter shaft along which the catheter shaft can be moved, the guide wire having a distal end;

a conical head pivotally connected to the distal end, the conical head having a solid exterior surface; and means coupled to the conical head for changing the direction of the conical head, the means being external to the guide wire along the entire length of the guide wire.

9. An instrument comprising:

a catheter shaft;

a guide wire received within the catheter shaft, along which the catheter shaft can be moved;

the guide wire having a distal end;

a conical head pivotally connected to an extending from the distal end of the guidewire;

a plurality of outer wires directly connected to the conical head and extending along the entire length of the guide wire, the outer wires being external to the guide wire along the entire length of the guide wire, for changing the direction of the conical head by the selective application of tension to at least one of the wires.

10. The instrument of claim 9, wherein the conical head has a solid exterior surface.

11. The instrument of claim 10, wherein the guide wire has a larger diameter than the outer wires.

12. The instrument of claim 10, further comprising means for establishing the position of the instrument by magnetic resonance imaging.

13. The instrument of claim 10, wherein the catheter further comprises means for delivering heat to an intended site within a patient, the delivering means being disposed within the catheter shaft.

14. The instrument of claim 10, wherein the catheter further comprises means for delivering radiation to an intended site within a patient, the delivering means being disposed within the catheter shaft.

15. The instrument of claim 10, wherein the catheter further comprises means for delivering a therapeutic chemical to an intended site within a patient, the delivering means being disposed within the catheter shaft.

16. The instrument of claim 10, further comprising an optical fiber received within the catheter shaft for permitting optical communication with a region within a patient to undergo treatment.

17. The instrument of claim 10, wherein the catheter further comprises means for delivering light to an intended site within a patient, the delivering means being disposed within the catheter shaft.

18. The instrument of claim 10, wherein the means for delivering light comprises an optical fiber and a laser optically coupled to the optical fiber for delivering light of sufficient intensity to effectuate treatment, through the optical fiber.

* * * * *

UNITED STATES PATENT AND TRADEMARK OFFICE
CERTIFICATE OF CORRECTION

PATENT NO. : 6,165,139
DATED : December 26, 2000
INVENTOR(S) : Raymond V. Damadian It is certified that error appears in the above-identified patent and that said Letters Patent is hereby corrected as shown below:

Column 12,
Line 22, change "10" to -- 9 --;
Line 24, change "10" to -- 9 --;
Line 27, change "10" to -- 9 --;
Line 31, change "10" to -- 9 --;
Line 35, change "10" to -- 9 --;
Line 39, change "10" to -- 9 --;
Line 43, change "10" to -- 9 --; and
Line 47, change "10" to -- 17 --.

Signed and Sealed this

Twenty-seventh Day of August, 2002

*Attest:*

*Attesting Officer*

JAMES E. ROGAN
*Director of the United States Patent and Trademark Office*